(12) United States Patent
Dunsmore et al.

(10) Patent No.: US 8,528,547 B2
(45) Date of Patent: Sep. 10, 2013

(54) HIGH FREQUENCY OSCILLATION RESPIRATORY THERAPY

(75) Inventors: Thomas J. Dunsmore, Glendora, CA (US); Thomas C. Wilschke, Chicago, IL (US); Geoffrey C. Wise, Benicia, CA (US)

(73) Assignee: CareFusion 2200, Inc., San Diego, CA (US)

( * ) Notice: Subject to any disclaimer, the term of this patent is extended or adjusted under 35 U.S.C. 154(b) by 1470 days.

(21) Appl. No.: 12/061,511

(22) Filed: Apr. 2, 2008

(65) Prior Publication Data

US 2008/0245368 A1      Oct. 9, 2008

Related U.S. Application Data

(60) Provisional application No. 60/291,414, filed on Apr. 2, 2007.

(51) Int. Cl.
*A61M 15/00* (2006.01)
*A61M 16/00* (2006.01)

(52) U.S. Cl.
USPC ................................. 128/203.12; 128/204.18

(58) Field of Classification Search
USPC .............. 128/200.14–200.22, 203.12–203.14
See application file for complete search history.

(56) References Cited

U.S. PATENT DOCUMENTS

| | | | |
|---|---|---|---|
| 2,071,215 A | 2/1937 | Petersen | |
| 2,918,917 A | 12/1959 | Emerson | |
| 3,068,856 A | 12/1963 | Bird et al. | |
| 3,191,596 A | 6/1965 | Bird | |
| 3,234,932 A | 2/1966 | Bird | |
| 3,301,255 A | 1/1967 | Thompson | |
| 3,537,448 A | 11/1970 | Liston | |
| 3,580,249 A | 5/1971 | Takaoka | |
| 3,581,742 A | 6/1971 | Glenn | |
| 3,584,621 A | 6/1971 | Bird et al. | |

(Continued)

FOREIGN PATENT DOCUMENTS

| EP | 1 516 640 A1 | 9/2004 |
|---|---|---|
| RU | 44253 | 3/2005 |

OTHER PUBLICATIONS

Fink et al., "High-Frequency Oscillation of the Airway and Chest Wall", Respiratory Care, 47(7):797-807 (Jul. 2002).

(Continued)

*Primary Examiner* — Justine Yu
*Assistant Examiner* — Rachel Young
(74) *Attorney, Agent, or Firm* — McDermott Will & Emery LLP (57) ABSTRACT

A respiratory therapy device including a housing, a flow diverter structure, a high frequency pressure port (HF port), and an entrainment port. The housing defines a primary passageway having a patient interface side. The flow diverter structure is in fluid communication with the primary passageway and is characterized by the absence of a venturi tube. The HF port is configured for fluid connection to a source of oscillatory gas flow, and is fluidly associated with the flow diverter structure. The entrainment port is openable to ambient air, and is fluidly associated with the flow diverter structure. With this construction, the device is configured such that flow characteristics of gas flow from an external source are altered upon interacting with the flow diverter structure to create a pressure drop for drawing in ambient air through the entrainment port in delivering a percussive pressure therapy to the patient side.

11 Claims, 7 Drawing Sheets

(56) References Cited

U.S. PATENT DOCUMENTS

| | | | |
|---|---|---|---|
| 3,610,237 A | 10/1971 | Barkalolw et al. | |
| 3,630,196 A | 12/1971 | Bird et al. | |
| 3,653,379 A | 4/1972 | Glenn | |
| 3,664,337 A | 5/1972 | Lindsey et al. | |
| 3,769,973 A | 11/1973 | Esbenshade, Jr. | |
| 3,881,480 A | 5/1975 | Lefourcade | |
| 3,903,884 A | 9/1975 | Houston | |
| 4,224,940 A | 9/1980 | Monnier | |
| 4,231,973 A | 11/1980 | Young et al. | |
| 4,323,064 A | 4/1982 | Hoenig et al. | |
| 4,351,329 A | 9/1982 | Ellestad et al. | |
| 4,471,773 A * | 9/1984 | Bunnell et al. | 128/204.21 |
| 4,592,349 A | 6/1986 | Bird et al. | |
| 4,719,910 A | 1/1988 | Jensen | |
| 4,805,612 A | 2/1989 | Jensen | |
| 4,805,613 A | 2/1989 | Bird | |
| 4,823,828 A | 4/1989 | McGinnis | |
| 4,838,260 A | 6/1989 | Bird | |
| 4,930,501 A | 6/1990 | Bird | |
| 5,007,420 A | 4/1991 | Bird | |
| 5,107,831 A | 4/1992 | Halpern et al. | |
| 5,116,088 A | 5/1992 | Bird | |
| 5,253,641 A | 10/1993 | Choate | |
| 5,345,930 A | 9/1994 | Cardinal et al. | |
| 5,479,920 A | 1/1996 | Piper et al. | |
| 5,570,682 A | 11/1996 | Johnson | |
| 5,598,839 A | 2/1997 | Niles et al. | |
| 5,613,489 A | 3/1997 | Miller et al. | |
| 5,655,520 A | 8/1997 | Howe et al. | |
| 5,868,802 A | 2/1999 | Akatani et al. | |
| 5,899,832 A | 5/1999 | Hougen | |
| 6,067,984 A | 5/2000 | Piper | |
| 6,102,038 A | 8/2000 | DeVries | |
| 6,152,130 A * | 11/2000 | Abrams et al. | 128/204.21 |
| 6,253,766 B1 | 7/2001 | Niles et al. | |
| 6,279,574 B1 | 8/2001 | Richardson et al. | |
| 6,340,025 B1 | 1/2002 | Van Brunt | |
| 6,355,002 B1 | 3/2002 | Faram et al. | |
| 6,557,549 B2 | 5/2003 | Schmidt et al. | |
| 6,581,596 B1 | 6/2003 | Truitt et al. | |
| 6,581,598 B1 | 6/2003 | Foran et al. | |
| 6,595,203 B1 | 7/2003 | Bird | |
| 6,595,213 B2 | 7/2003 | Bennarsten | |
| 6,606,989 B1 | 8/2003 | Brand et al. | |
| 6,631,721 B1 | 10/2003 | Salter et al. | |
| 6,659,100 B2 | 12/2003 | O'Rourke | |
| 6,694,978 B1 | 2/2004 | Bennarsten | |
| 6,705,316 B2 | 3/2004 | Blythe et al. | |
| 6,708,690 B1 | 3/2004 | Hete et al. | |
| 6,776,159 B2 | 8/2004 | Pelerossi et al. | |
| 6,848,443 B2 | 2/2005 | Schmidt et al. | |
| 6,904,906 B2 | 6/2005 | Salter et al. | |
| 6,929,007 B2 | 8/2005 | Emerson | |
| 7,000,610 B2 | 2/2006 | Bennarsten et al. | |
| 7,059,324 B2 | 6/2006 | Pelerossi et al. | |
| 7,191,780 B2 | 3/2007 | Faram | |
| 2003/0000531 A1 | 1/2003 | Tuck | |
| 2003/0005931 A1 | 1/2003 | Jaffre et al. | |
| 2003/0051729 A1 | 3/2003 | Be'eri et al. | |
| 2003/0127092 A1 | 7/2003 | Pelerossi et al. | |
| 2005/0061318 A1 | 3/2005 | Faram | |
| 2006/0011198 A1 | 1/2006 | Matarasso | |
| 2006/0090753 A1 | 5/2006 | Pelerossi et al. | |
| 2007/0023036 A1 | 2/2007 | Grychowski et al. | |
| 2007/0023050 A1 * | 2/2007 | Janatpour | 128/207.15 |
| 2008/0262377 A1 * | 10/2008 | Belson | 600/549 |

OTHER PUBLICATIONS

Kim et al., "Mucus Clearance by Two-Phase Gas-Liquid Flow Mechanism: Asymmetric Periodic Flow Model", J. Appl. Physiol., 62(3):959-971 (Mar. 1987).

Russian Official Decision on Grant—Translation RU 2009140311 dated Sep. 27, 2011 (6 pages).

International Preliminary Report on Patentability dated Oct. 6, 2009 (6 pages).

Written Opinion of the International Searching Authority dated Aug. 28, 2008 (5 pages).

International Search Report dated Aug. 28, 2008 (1 page).

* cited by examiner

HIGH FREQUENCY OSCILLATION RESPIRATORY THERAPY

CROSS-REFERENCE TO RELATED APPLICATIONS

This application claims priority under 35 U.S.C. §119(e)(1) to U.S. Provisional Patent Application Ser. No. 60/291,414, filed Apr. 2, 2007, entitled "Continuous High Frequency Oscillation Respiratory Therapy Device,"; the entire teachings of which are incorporated herein by reference.

BACKGROUND OF THE INVENTION

The present invention relates to respiratory therapy devices. More particularly, it relates to percussive respiratory devices that deliver high frequency pulses of air to a patient during the patient's inspiratory and expiratory cycles.

A wide variety of respiratory therapy devices are currently available for assisting, treating, or improving a patient's respiratory health. For example, positive airway pressure (PAP) has long been recognized to be an effective tool in promoting bronchial hygiene by facilitating improved oxygenation, increased lung volumes, and reduced venous return in patients with congestive heart failure. More recently, positive airway pressure has been recognized as useful in promoting mobilization and clearance of secretions (e.g., mucus) from a patient's lungs. In this regard, positive airway pressure in the form of high frequency oscillation (HFO) of the patient's air column is a recognized technique that facilitates secretion removal. In general terms, HFO reduces the viscosity of sputum in vitro, which in turn has a positive effect on clearance induced by an in vitro simulated cough. HFO can be delivered or created via a force applied to the patient's chest wall (i.e., chest physical therapy (CPT), such as an electrically driven pad that vibrates against the patient's chest), or by applying forces directly to the patient's airway (i.e., breathing treatment, such as high frequency airway oscillation). Many patients and caregivers prefer the breathing treatment approach as it is less obtrusive and more easily administered. To this end, PAP bronchial hygiene techniques have emerged as an effective alternative to CPT for expanding the lungs and mobilizing secretions.

Various treatment systems are available for providing the respiratory therapy described above (as well as other therapies and/or ventilation). For example, intrapulmonary percussive ventilation (IPV) therapy relates to HFO devices that deliver pulses of air into the patient's airway opening. In general terms, an IPV system includes a hand-held device establishing a patient breathing circuit to which a source of positive pressure gas (e.g., air, oxygen, etc.), is fluidly connected. The pressure source and/or the device further include appropriate mechanisms (e.g., control valves provided as part of a driver unit apart from the hand-held device) that effectuate intermittent flow of gas into the patient breathing circuit, and thus percussive ventilation of the patient's lungs. With this approach, the patient breathes through a mouthpiece that delivers high-flow, "mini-bursts" of gas. During these percussive bursts, a continuous airway pressure above ambient is maintained, while the pulsatile percussive gas flow periodically increases airway pressure (e.g., the gas flow cycles the delivered pressure). Each percussive cycle can be programmed by the patient or caregiver with certain systems, and can be used throughout both inspiratory and expiratory phases of the breathing cycle. Examples of IPV devices include IPV® ventilator device (from PercussionAire Corp. of Sandpoint, Id.), IMP 2™ (from Breas Medical of Molnlycke, Sweden), and PercussiveNeb™ System (from Vortran Medical Technology, Inc., of Sacramento, Calif.). Also, U.S. Pat. No. 7,191,780 describes an IPV-type treatment apparatus, connectable to a source of pressurized gas, that requires a shrouded, fixed venturi tube for delivering the desired therapy.

In light of the promising nature of IPV therapy devices, any improvements to known designs, such as enhanced performance, long-term reliability, reduced manufacturing costs, ease of operation, etc., will be well received.

SUMMARY

Some aspects in accordance with the principles of the present disclosure relate to a respiratory therapy device including a housing, a flow diverter structure, a high frequency pressure port (HF port), and an entrainment port. The housing defines a primary passageway having a patient interface side. The flow diverter structure is maintained by the housing in fluid communication with the primary passageway opposite the patient interface side. In this regard, the flow diverter structure is characterized by the absence of a venturi tube. The HF port is maintained by the housing and is configured for fluid connection to a source of oscillatory gas flow. Further, the HF port is fluidly associated with the flow diverter structure. The entrainment port is also maintained by the housing, is openable to ambient air, and is fluidly associated with the flow diverter structure. With this construction, the device is configured such that flow characteristics of gas flow from an external source are altered upon interacting with the flow diverter structure to create a pressure drop for drawing in ambient air through the entrainment port in delivering a percussive pressure therapy to the patient side of the primary passageway. In some embodiments, the HF port is connected to or forms a nozzle having a nozzle end that faces the flow diverter structure, with the flow diverter structure including a neck region forming a reduced-size passage immediately adjacent the primary passageway. In other embodiments, the device further includes a continuous positive pressure port (CPP port) configured for fluid connection to a source of continuous positive pressure gas flow. With this construction, the flow diverter structure moves in response to pressure pulses delivered via the HF port in affecting gas flow from the CPP port toward the primary passageway. Alternatively, the CPP port can be the same port as the HF port in some constructions.

Other aspects in accordance with principles of the present disclosure relate to a respiratory therapy system including a source of oscillatory gas flow and a respiratory therapy device. The respiratory therapy device includes the housing, flow diverter structure, HF port, and entrainment port as described above. The source of oscillatory gas flow is fluidly connected to the HF port. During operation of the system, oscillatory gas flow from the source is delivered to the respiratory therapy device and impacted by the flow diverter structure to cause entrainment of ambient air with the pressure pulses delivered to the patient interface side, and thus the patient.

Yet other aspects in accordance with principles of the present disclosure relate to a respiratory therapy device including a housing, a continuous positive pressure port (CPP port), a flow diverter structure, a high frequency pressure port (HF port), and an entrainment port. The housing defines a primary passageway having a patient interface side. The CPP port is maintained by the housing and is configured for fluid connection to a source of continuous positive pressure gas flow. The flow diverter structure includes an obstruction body movably maintained within the housing, fluidly between the CPP port and the primary passageway. The HF port is also maintained by the housing and is fluidly connected to the flow diverter structure. Further, the HF port is configured for fluid connection to a source of oscillatory gas flow such that a pressure pulse delivered to the HF port causes movement of the obstruction body. Finally, the entrainment port is maintained by the housing and is openable to ambient air, with the entrainment port being fluidly associated with the flow diverter structure. With the above construction, the device is configured such that flow characteristics of gas flow from the CPP port are selectively altered upon interaction with the obstruction body to deliver a percussive pressure therapy to the patient interface side of the primary passageway. In some embodiments, the obstruction body is longitudinally movable relative to a central axis of the CPP port. In other embodiments, the obstruction body is rotatably mounted within the housing.

DETAILED DESCRIPTION

Figure 1:
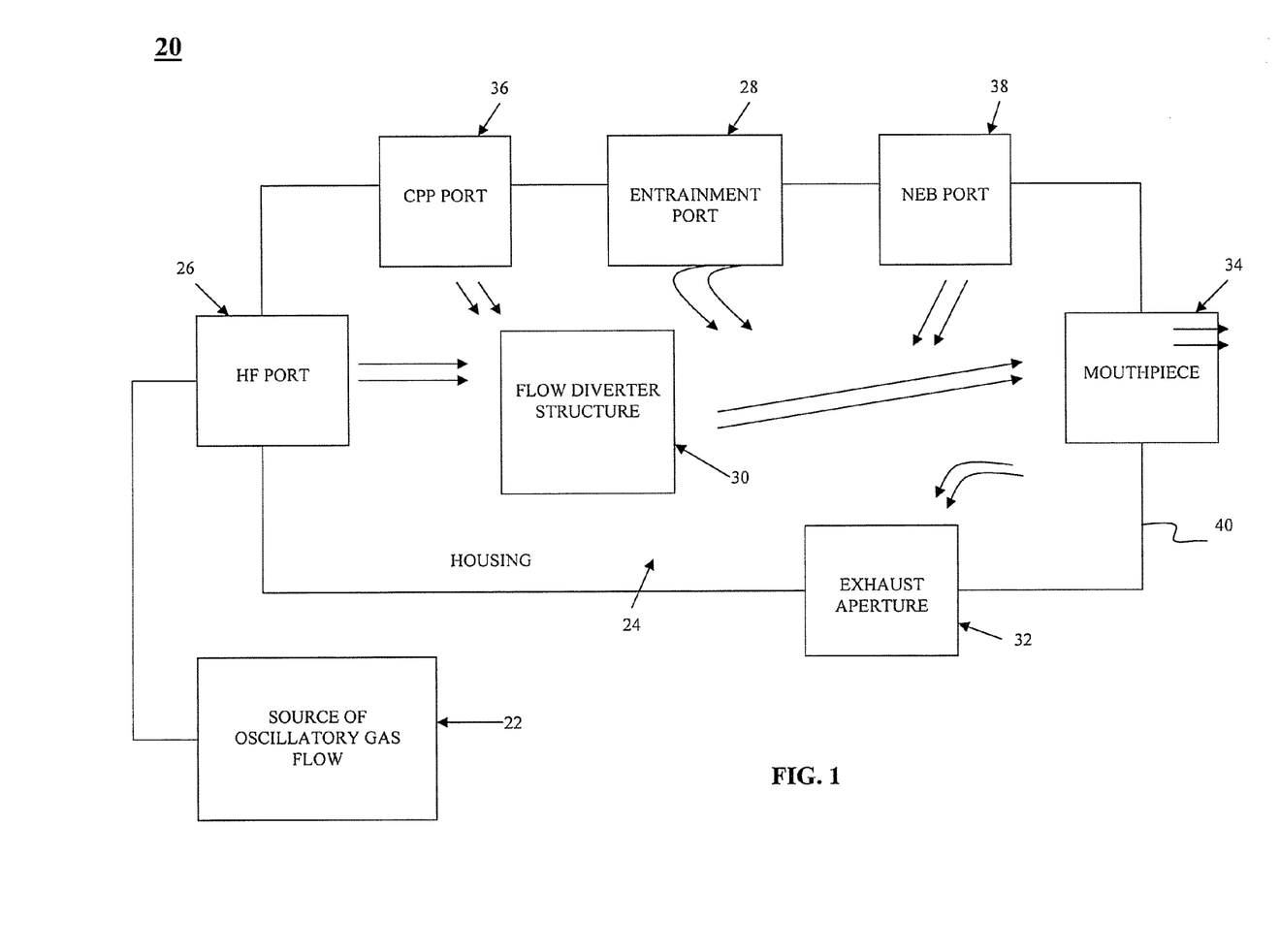
FIG. 1 is a block diagram of a percussive respiratory therapy device in accordance with aspects of the present disclosure.

General features of a respiratory therapy device 20 in accordance with aspects of the present disclosure is shown in block form in FIG. 1. In general terms, the respiratory therapy device 20 operates to deliver high frequency pulses of air to a patient during the patient's inspiratory and expiratory cycles when connected to a source of oscillatory gas flow 22. In this regard, the source of oscillatory gas flow 22 can assume a variety of forms known in the art, and generally includes a flow interrupter valve or similar structure capable of generating an oscillatory flow of positive pressure gas (e.g., air, oxygen, etc.), such as that described in U.S. Pat. No. 4,805,613, the teachings of which are incorporated herein by reference. In other embodiments, the therapy device 20 can be configured to establish an oscillatory flow when acting upon a constant flow of gas such that the source 22 can be a source of constant gas flow. With this in mind, the respiratory therapy device 20 includes a housing 24 maintaining and/or forming various components such as a high frequency flow port (HF port) 26, one or more entrainment ports 28, a flow diverter structure 30, one or more exhaust apertures 32, and a mouthpiece 34. In addition, the respiratory therapy device 20 can optionally include a constant positive pressure port (CPP port) 36 and/or a nebulizer port 38.

Details on the various components are provided below in connection with embodiments being described. In general terms, however, the flow diverter structure 30 in accordance with the present disclosure can assume a variety of forms as described below, and in some embodiments is generally characterized as not being or including a venturi tube (fixed or sliding), where a "venturi tube" is defined to be a body including a gradually decreasing or converging diameter nozzle section that extends to a throat, followed by a gradually increasing or expanding diameter diffuser section. The flow diverter structure 30 is fluidly connected to a primary passageway formed by the housing 24, as is the mouthpiece 34. The mouthpiece 34 serves as a patient interface through which the patient breathes and can assume a variety of forms. In more general terms, then, the primary passageway of the housing 24 can be defined as having a patient interface side 40 at which the mouthpiece 34 is connected.

During use, high frequency oscillatory gas flow is directed from the source 22 to the HF port 26 and then toward the flow diverter structure 30 (represented by arrows in FIG. 1). High velocity flow from the HF port 26 (e.g., a nozzle) creates a pressure drop within the housing 24 that, in turn, entrains ambient air via the entrainment port(s) 28. Interaction between high velocity flow and the flow diverter structure 30 causes gas flow to be directed toward the mouthpiece 34. In some embodiments, the flow diverter structure 30 operates to affect gas flow from the HF port 24 in a pulse-like manner, creating a percussive gas flow/pressure effect toward the mouthpiece 34. With these embodiments, then, a constant input pressure flow to the housing 24 can be used, thus eliminating a need for the source of oscillatory gas flow 22. In other embodiments, the flow diverter 30 operates in response to delivered oscillatory gas flow, in turn acting upon a separate, constant flow of gas to generate oscillatory pressure pulses that are delivered to the mouthpiece 34/patient. Regardless, oscillatory pressure pulses (including entrained ambient air) are delivered to the patient via the mouthpiece 34. Between pulses, the exhaust aperture(s) 32 and the entrainment port(s) 28 allow the patient to breathe in and out of the device 20 without significant resistance.

Where provided, the CPP port 36 can be connected to a source of positive pressure gas (not shown) to enhance the respiratory therapy provided by the device 20 (e.g., generate appropriate positive expiratory pressure (PEP), etc.), provide a primary gas flow that is acted upon by the flow diverter 30, and/or to provide other therapies (e.g., constant positive airway pressure (CPAP)). Similarly, the optional nebulizer port 38 can be connected to a nebulizer (not shown) to introduce aerosolized medication into the gas flow delivered to the patient. In some embodiments, the nebulizer port 38 is physically positioned between the flow diverter structure 30 and the mouthpiece 34 such that the aerosolized airflow does not directly interact with the flow diverter structure 30 in a manner that might otherwise result in undesirable aerosol "knockdown".

Figure 2:
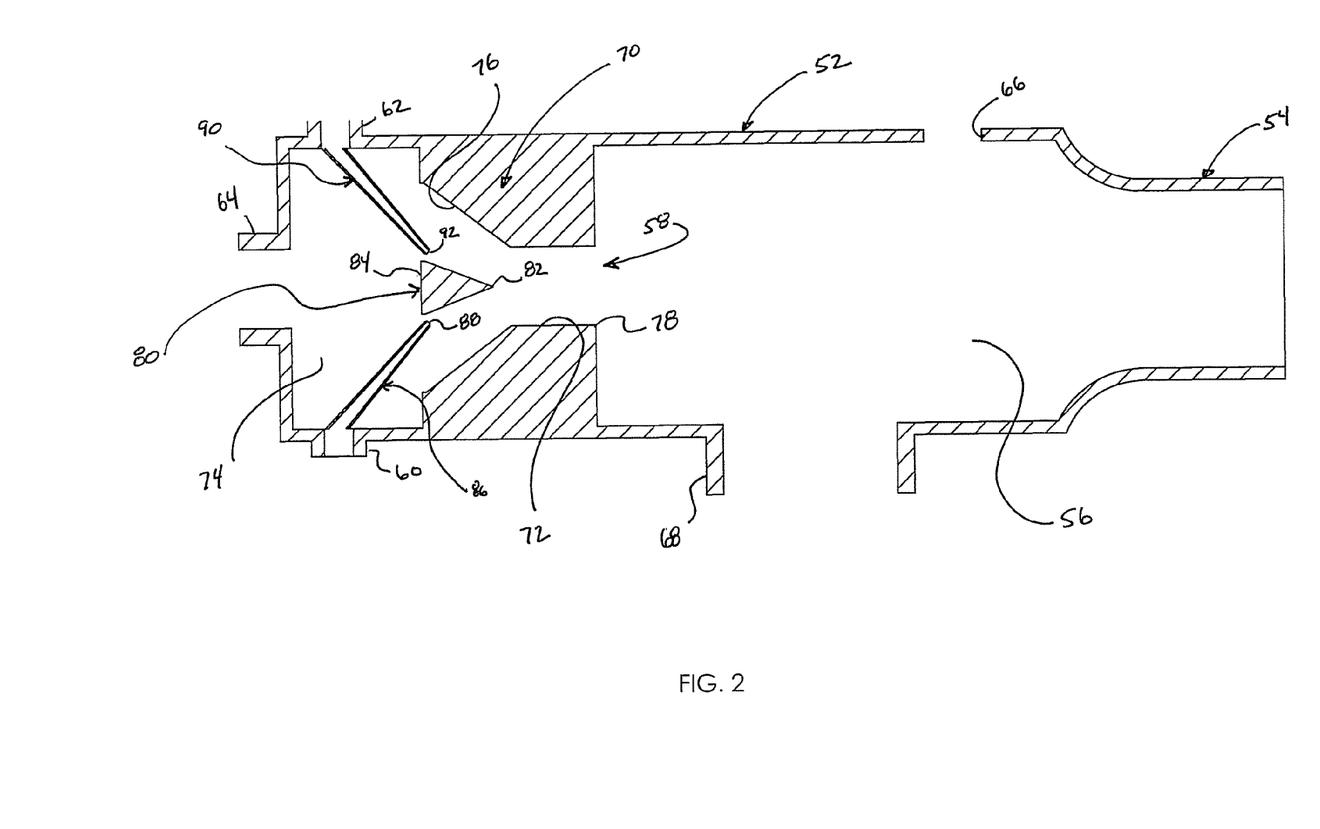
FIG. 2 is a simplified, cross-sectional illustration, with portions drawn schematically, of one embodiment of a respiratory therapy device.

With the above general construction in mind, FIG. 2 schematically illustrates one embodiment of a respiratory therapy device 50 in accordance with principles of the present disclosure. The device 50 includes a housing 52 maintaining or connectable to a mouthpiece 54 (referenced generally) adapted for placement in a patient's mouth and through which the patient can breathe. The housing 52 further forms a primary passageway 56 through which gas flow from a flow diverter structure 58 is fluidly directed to the mouthpiece 54. In this regard, the housing 52 further includes or forms an HF port 60, a CPP port 62, and one or more entrainment ports 64. Gas flow through the ports 60-64 is directed to the flow diverter structure 58. Finally, the device 50 optionally includes one or more exhaust apertures 66 and/or a nebulizer port 68. As described below, the exhaust aperture 66 and the nebulizer port 68 can be combined and/or provided as part of a singular structure that may include one or more additional valves.

The flow diverter structure 58 includes, in some embodiments, a neck region 70 formed in or by the housing 52. The neck region 70 defines a reduced-size passage 72, and fluidly connects the primary passageway 56 with a chamber 74. More particularly, the reduced-size passage 72 has a smaller cross-sectional area (e.g., diameter) as compared to that of the chamber 74 and the primary passageway 56. The reduced-size passage 72 is defined by an inlet side 76 and an outlet side 78. As shown in FIG. 2, the inlet side 76 tapers in cross-sectional area (or diameter) from the chamber 74 at which the ports 60-64 are formed. The outlet side 78 has a constant diameter in extension from the inlet side 76 to the primary passageway 56. In addition, the flow diverter structure 58 can include a diverter body 80 centrally positioned within the reduced-size passage 72, adjacent the inlet side 76. The diverter body 80 includes or defines a leading end 82 and a trailing end 84, with the diverter body 80 tapering in size or diameter from the trailing end 84 to the leading end 82. With this construction, the diverter body 80 affects airflow from the HF port 60 and the CPP port 62 as described below. In other embodiments, the diverter body 80 can be eliminated.

The HF port 60 is adapted to be fluidly connected to the source of oscillatory gas flow 22 (FIG. 1), for example via appropriate tubing (not shown). In addition, the HF port 60 is fluidly connected to or forms an HF nozzle 86. The HF nozzle 86 terminates at a nozzle end 88, and is configured to generate jet gas flow. In this regard, the nozzle end 88 "faces" the diverter body 80 such that jet flow from the HF port 60 (and thus from the source of oscillatory gas flow 22) impinges upon the diverter body 80.

The CPP port 62 is similarly constructed for fluid connection to a source of continuous or constant positive pressure gas (not shown). The CPP port 62 is fluidly connected to or forms a CPP nozzle 90 terminating at a nozzle end 92. The CPP nozzle 90 converts gas flow through the CPP port 62 into jet flow, with the nozzle end 92 "facing" the diverter body 80. Thus, gas flow through and from the CPP nozzle 90 impinges upon the diverter body 80.

The entrainment port(s) 64 is, in some embodiments, formed along the chamber 74, and allows for passage of gas into and out of the chamber 74, and thus the housing 52. In this regard, the entrainment port(s) 64 is fluidly associated with the flow diverter structure 58 to promote entrainment of ambient air into the gas flow otherwise generated at the flow diverter structure 58. In other embodiments, the entrainment port(s) 64 can be located at other locations relative to the housing 52. For example, the entrainment port(s) 64 can be formed or located along the neck region 70.

With the above configuration, the nozzles/jets 86, 90 converge at or along the flow diverter structure 58. Thus, and as described below, the flow diverter structure 58 ensures that gas flow streams from the nozzles 86, 90 are directed toward the primary passageway 56 (and thus the patient) and that adequate ambient air entrainment (via the entrainment port(s) 64) is produced.

The exhaust aperture 66 can simply be an orifice formed in the housing 52 adjacent the mouthpiece 54, establishing an ambient opening to the primary passageway 56. In some embodiments, a valve (not shown), such as a one-way valve, can be assembled to the exhaust aperture 66, operating to selectively control gas flow to and/or from the primary passageway 56. For example, the valve can operate to only permit release of gas from the primary passageway 56 during a patient's expiratory breath.

Where provided, the nebulizer port 68 is adapted for connection to a nebulizer (not shown), such as a high-performance entrainment nebulizer available under the trade designation Pari LC Star, although any other nebulizer arrangement capable of generating aerosolized medication can be employed. Regardless, the nebulizer port 68 is formed adjacent the mouthpiece 54 (and thus "downstream" of the flow diverter structure 58). With this positioning, aerosolized entrainment within the gas flow being delivered to the mouthpiece 54/patient can occur without resulting in significant aerosol knock-down within the flow diverter structure 58. Further, a one-way valve (not shown) can be provided to ensure desired airflow from the nebulizer into the primary passageway 56. Alternatively, the nebulizer, and thus the nebulizer port 68, can be eliminated.

Figure 3A:
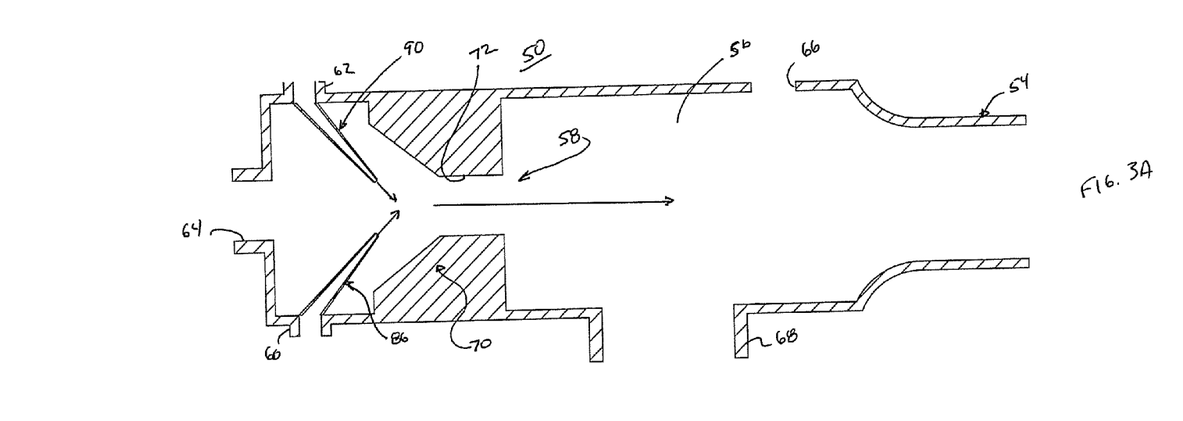
FIGS. 3A and 3B are simplified, cross-sectional illustrations, with portions drawn schematically, of an alternative configuration of the device of FIG. 2 and showing use thereof in generating a percussive therapy.
Figure 3B:
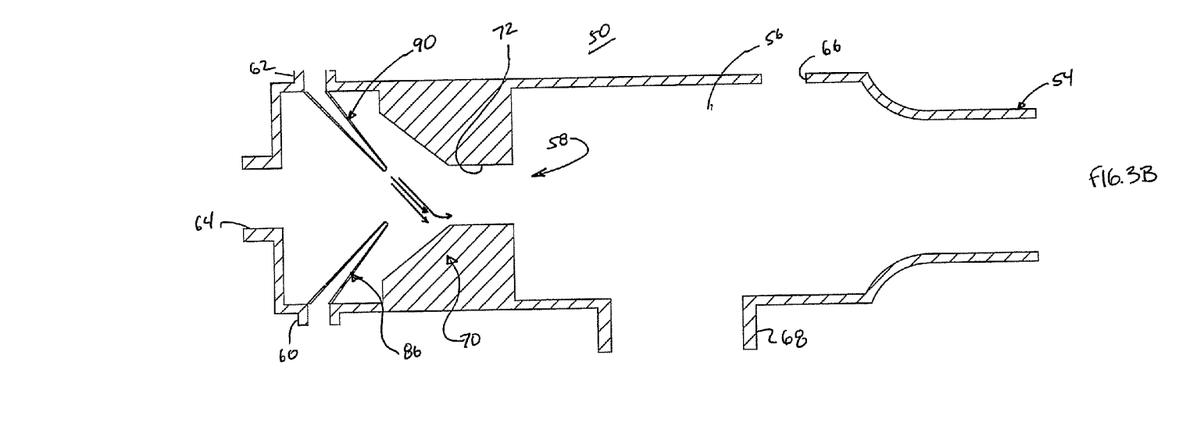

Operation of the respiratory therapy device 50 is shown in the illustrations of FIGS. 3A and 3B. A constant flow of positive pressure gas is delivered to the flow diverter structure 58 via the CPP nozzle 90. Similarly, oscillatory (i.e., pulsed) gas flow is provided to the flow diverter structure 58 via the HF nozzle 86. In this regard, gas flow through the HF nozzle 86 (as created, for example, by the source of oscillatory gas flow 22 (FIG. 1)) is characterized as being intermittent positive-pressure pulses, and thus has "pulse on" and "pulse off" phases. During the "pulse on" phase (FIG. 3A), gas flow from the HF nozzle 86 and the CPP nozzle 90 converge at the flow diverter structure 58, and are directed along the reduced-size passage 72 and then the primary passageway 56 (shown by arrows in FIG. 3A). Due to the reduced area at the reduced-size passage 72 (as compared to an area of the chamber 74 and the primary passageway 56), the so-delivered gas flow increases in velocity along the reduced-size passage 72, thus drawing or entraining ambient air into the gas stream via the entrainment port(s) 64. Where the diverter body 80 (FIG. 2) is provided, a further reduction in flow area, and thus increase in velocity is created. In the "pulse off" phase (FIG. 3B), gas flow to the flow diverter structure 58 is provided only by the CPP nozzle 90. Once again, however, the flow diverter structure 58 directs the gas flow along the reduced-size passage 72 and to the primary passageway 56 such that ambient air is entrained via the entrainment port(s) 64 as described above. As a result, an elevated baseline pressure is provided to the patient on a continuous basis. By providing the CPP flow (via the CPP nozzle 90), flow towards the patient continues to occur during the "pulse off" phase, and thus serves to maintain the elevated baseline pressure during high frequency oscillatory therapy.

Other respiratory therapies can also be effectuated with the device 50. For example, gas flow through the CPP nozzle 90 can be removed where high frequency oscillatory therapy without an elevated baseline pressure is desired. Conversely, gas flow via the HF nozzle 86 can be omitted where only constant positive airway pressure (CPAP) therapy is desired.

During the delivery of high frequency oscillatory pressure therapy, the patient breathes into and out of the therapy device 50 via the mouthpiece 54. In this regard, the entrainment port(s) 64 and the exhaust aperture(s) 66 (in combination with a one-way valve, in some embodiments) allows the patient to breathe into and out of the device 50 without significant resistance during at least the "pulse off" phase.

Throughout the delivery of high frequency oscillatory flow, aerosolized medication can be introduced into the flow stream at the primary passageway 56 via the nebulizer port 68. As described above, aerosolized flow is entrained into the gas flow generated in the primary passageway 56 by the flow diverter structure 58 and thus delivered to the patient via the mouthpiece 54.

Figure 4:
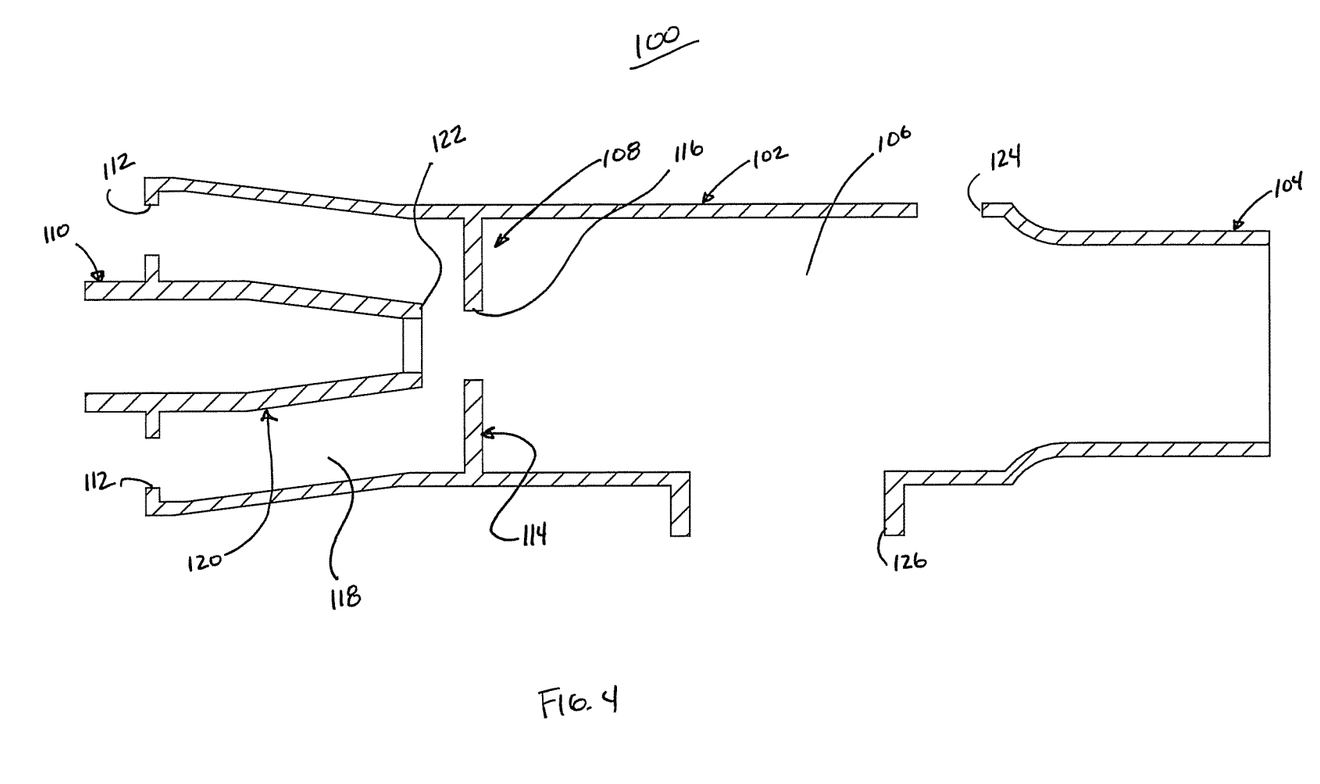
FIG. 4 is a simplified, cross-sectional illustrations, with portions drawn schematically, of another embodiment respiratory therapy device.

Yet another embodiment of a respiratory therapy device 100 is shown schematically in FIG. 4. As with previous embodiments, the device 100 includes a housing 102 maintaining or forming or connectable to a mouthpiece 104 (drawn generally) through which a patient breathes. The housing 102 establishes a primary passageway 106 through which airflow into and out of the mouthpiece 104 is directed. In this regard, HF flow into the primary passageway 106 is established via a flow diverter structure 108 formed opposite the mouthpiece 104 and fluidly associated with an HF port 110 and one or more entrainment ports 112.

With the configuration of FIG. 4, the flow diverter structure 108 includes a plate 114 that forms an orifice 116. The plate 114 is positioned or formed within the housing 102 so as to establish or define a chamber 118 opposite the primary passageway 106, with the orifice 116 fluidly connecting the passageway 106 and the chamber 118. The orifice 116 has an area (i.e., diameter) that is less than that of the chamber 118 as well as the passageway 106. Further, a diameter of the orifice 116 is uniform through a thickness of the plate 114 in some configurations. Although only the single orifice 116 is shown in FIG. 4, in other embodiments, the plate 114 can form two or more orifices.

The HF port 110 is associated with the chamber 118, and is configured for establishing a fluid connection with the source of oscillatory gas flow 22 (FIG. 1). Further, the HF port 110 is fluidly connected to or forms a nozzle 120 terminating at a nozzle end 122. As with previous embodiments, the HF nozzle 120 is configured to establish jet flow of gas, and the nozzle end 122 is generally aligned with or "faces" the orifice 116. As shown, at least a slight gap exists between the nozzle end 122 and the plate 114/orifice 116.

The entrainment port(s) 112 establishes a fluid opening between the chamber 118 and ambient air. While the entrainment port(s) 112 is shown as being formed adjacent the HF port 110, any other location in fluid communication with the chamber 118 is also acceptable.

With the above construction, oscillatory gas flow is delivered to the HF port 110 and the "pulsed on" flow is directed by the nozzle end 122 toward the orifice 116. Due to the reduced size of the orifice 116 (as compared to an area of the chamber 118), a pressure drop is generated within the chamber 118 as gas flow from the nozzle end 122 passes through the orifice 116. In other words, the reduced size of the orifice 116 increases the velocity of gas flowing therethrough, thus lowering the surrounding pressure to generate the pressure drop. The pressure drop, in turn, draws and entrains ambient air into the gas stream via the entrainment port(s) 112. As a result, a substantial volume of high frequency pulsed gas flow is delivered to the primary passageway 106, and thus the mouthpiece 104/patient.

To facilitate the inspiratory and expiratory phases of the patient's breaths, the device 100 can further include one or more exhaust apertures 124. Between pulses of the high frequency oscillating gas flow being generating within the primary passageway 106, the exhaust aperture(s) 124 and the entrainment port(s) 112 allow the patient to breathe into and out of the device 100 without significant resistance. Optionally, a valve structure (not shown), such as a one-way valve, can be assembled to the exhaust aperture(s) 124.

Finally, the respiratory therapy device 100 can include an optional nebulizer port 126 adapted for connection to a nebulizer (not shown). As with previous embodiments, the nebulizer port 126 is preferably located along the primary passageway 106, between the flow diverter structure 108 and the mouthpiece 104. With this position, aerosolized medication being delivered to the primary passageway 106 (and thus entrained within the gas flow being delivered to the mouthpiece 104/patient) is not required to pass through the flow diverter structure 108 (or any other structure that might otherwise result in significant aerosol knock-down). Further, although not shown, a valve mechanism can be associated with the nebulizer port 126, operating to allow influx of aerosolized medication via the nebulizer port 126 during only the patient's inspiratory breath and/or between the oscillatory pulses that occur during a patient's inspiratory breath. In this regard, the entrainment port(s) 112 and the exhaust aperture(s) 124 can be balanced with the nebulizer valve (and/or appropriate valving can be placed on the entrainment port(s) 112 and/or the exhaust aperture(s) 124) to ensure "activation" of nebulizer entrainment during the patient's inspiratory breath and/or between the oscillatory pulses that occur during a patient's inspiratory breath.

Figure 5:
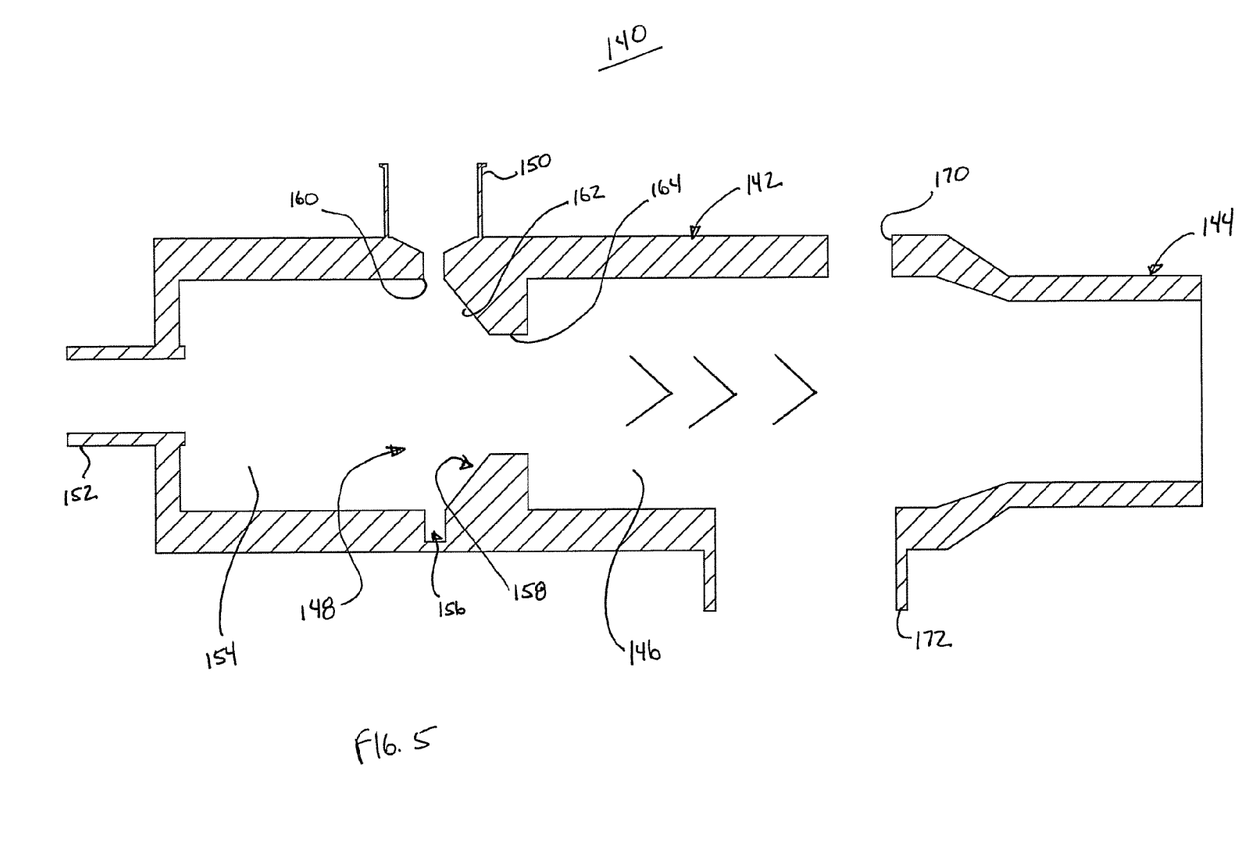
FIG. 5 is a simplified, cross-sectional illustration, with portions drawing schematically, of another embodiment respiratory therapy device.

Yet another embodiment of a respiratory therapy device 140 is shown in FIG. 5. The device 140 includes a housing 142 maintaining or forming or connectable to a mouthpiece 144 (drawn generally) through which a patient can breathe. The housing 142 forms a primary passageway 146 through which gas flow to and from the mouthpiece 144 is established. A flow diverter structure 148 (referenced generally) is fluidly connected to the primary passageway 146 opposite the mouthpiece 144, with gas flow being directed to the flow diverter structure 148 via an HF port 150. In addition, the housing 142 forms or includes one or more entrainment ports 152 through which ambient air is drawn into and entrained with the flow stream generated at the flow diverter structure 148.

The flow diverter structure 148 separates the primary passageway 146 from a chamber 154, and includes a ring orifice 156 and a neck region 158. The ring orifice 156 is fluidly connected to the HF port 150, and establishes an encircling opening 160 to the chamber 154. Thus, gas flow from the HF port 150 is directed into the chamber 154 via the ring orifice 156.

The neck region 158 includes an inlet portion 162 and a reduced-size passage 164. The inlet portion 162 has a tapering diameter in extension from the chamber 154 (and more particularly, the opening 160 of the ring orifice 156) to the reduced-size passage 164. As described below, this relationship promotes formation of a Coanda effect upon gas flow exiting the ring orifice 156. The reduced-size passage 164 has a uniform diameter in extension from the inlet portion 162 to the primary passageway 146, with a diameter of the reduced-size passage 164 being less than that of the chamber 154 and the primary passageway 146 such that gas flow experiences an increase in velocity when directed from the chamber 154 to the primary passageway 146.

The HF port 150 is configured for fluid attachment to the source of oscillatory gas flow 22 (FIG. 1), and is fluidly open to the ring orifice 156 as described above. The entrainment port(s) 152 can be positioned at a "back" of the chamber 154, or can be spatially closer to the flow diverter structure 148.

During use, oscillatory gas flow is provided to the ring orifice 156 via the HF port. As the pulses of oscillatory flow exiting the orifice opening 160 interact with the inlet portion 162, a Coanda effect is created, causing the flow to "attach" to the inlet portion 162 and be forced toward the reduced-size passage 164. Additionally, as the so-directed gas flow then passes through the reduced-size passage 164, flow velocity increases (due to the reduced area or diameter of the passage 164 as compared to the chamber 154), generating a pressure drop in the chamber 154. The pressure drop, in turn, draws ambient air through the entrainment port 152. As a result, significant entrainment of ambient air into the gas flow delivered to the primary passageway 146 occurs. In this regard, the gas flow delivered to the primary passageway 146 has oscillating pressure characteristics reflected in FIG. 5 by waves.

To facilitate ease of patient breathing, the respiratory therapy device 140 can further include an optional exhaust aperture 170 that fluidly connects the primary passageway 146 with ambient. With this configuration, between pulses of gas flow being delivered to the HF port 150, the exhaust aperture 170 and the entrainment port 152 effectively allow the patient to breathe in and out of the device 140 without significant resistance. An optional valving structure (not shown) can be assembled to the exhaust aperture 170.

The respiratory therapy device 140 can further include an optional nebulizer port 172 adapted for fluid connection to a nebulizer (not shown) as previously described. Once again, the nebulizer port 172 is fluidly open to the primary passageway 146, and can be positioned or formed between the mouthpiece 144 and the flow diverter structure 148 so as to minimize interaction between the aerosolized medication and the flow diverter structure 148. Regardless, where provided, the nebulizer port 172 provides a conduit through which aerosolized medication can be entrained into the gas flow being delivered to the patient via the mouthpiece 144. Though not shown, additional valving structures can be associated with the nebulizer port 172 to enhance efficiency of aerosol delivery. The entrainment port(s) 152 and the exhaust aperture 170 can be balanced with the nebulizer entrainment valve (or other valving) to ensure that nebulizer entrainment is "activated" during the patient's inspiratory breath and between the oscillatory pulses that occur during a patient's inspiratory breath.

Figure 6A:
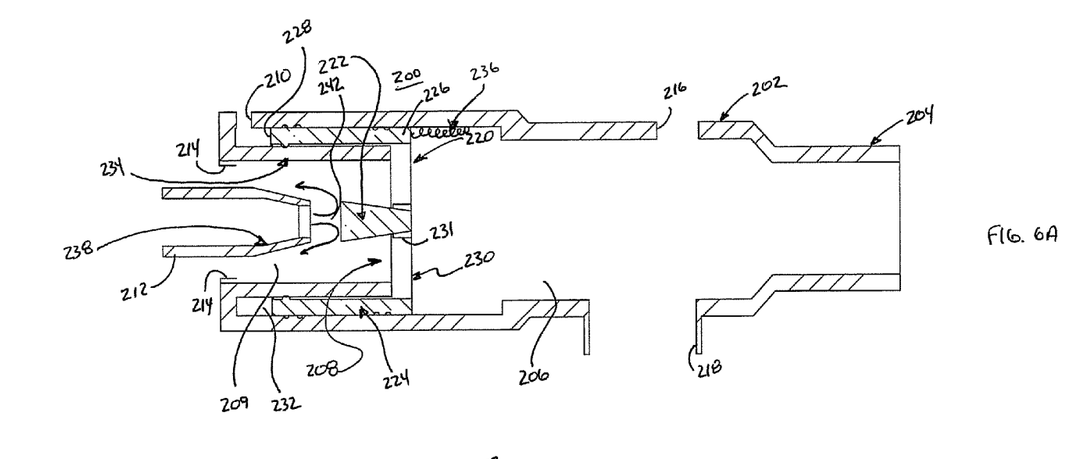
FIGS. 6A and 6B are simplified, cross-sectional illustrations, with portions drawn schematically, of another embodiment respiratory therapy device.
Figure 6B:
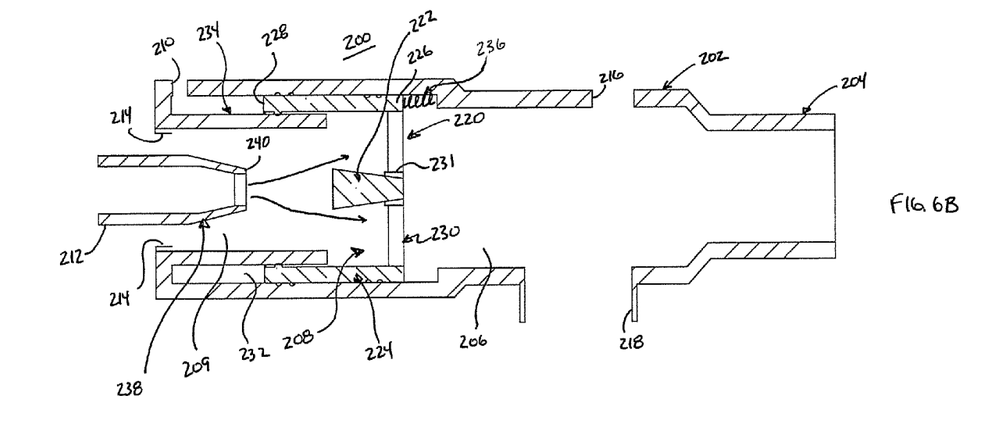

Another embodiment of a respiratory therapy device 200 in accordance with aspects of the present disclosure is shown in FIGS. 6A and 6B. The device 200 again includes a housing 202 forming or maintaining or connectable to a mouthpiece 204 (illustrated generally) through which a patient breathes. In this regard, gas flow to and from the mouthpiece 204 is provided via a primary passageway 206 defined by the housing 202. A flow diverter structure 208 is fluidly connected to the primary passageway 206 opposite the mouthpiece 204, the flow diverter structure 208 separating the primary passageway 206 from a chamber 209. The flow diverter structure 208 operates in response to gas flow at an HF port 210 to affect gas flow directed to the chamber 209/flow diverter structure 208 via a CPP port 212. In addition, the housing 202 forms or includes one or more entrainment ports 214 through which ambient air is drawn into and entrained with the flow stream generated at the flow diverter structure 208. Finally, the housing 202 optionally forms or includes one or more exhaust apertures 216 and/or a nebulizer port 218. As with previous embodiments, the nebulizer port 218, where provided, can be positioned adjacent the mouthpiece 204 and thus fluidly "downstream" of the flow diverter structure 208 to minimize aerosol knock-down.

With the therapy device 200 of FIGS. 6A and 6B, the flow diverter structure 208 includes a baffle device 220 slidably maintained within the housing 202. The baffle device 220 includes or forms an obstruction body 222 fluidly associated with the CPP port 212. More particularly, the baffle device 220 operates to move the obstruction body 222 toward and away from the CPP port 212, thus altering the level of gas flow entering the primary passageway 206 from the chamber 209/CPP port 212, as well as the volume of ambient air entrained therein via the entrainment port(s) 214. In this regard, the obstruction body 222 can have a variety of different geometries selected to affect gas flow from the CPP port 212 as desired. Thus, the conical shape accorded to the obstruction body 222 in FIGS. 6A and 6B is but one, non-limiting example.

The baffle device 220 can be configured in a variety of fashions to provide the above-described movement. For example, in one embodiment, the baffle device 220 includes an annular hub 224 having a leading end 226 and a trailing end 228. A radial support 230 extends from the leading end 226 and maintains the obstruction body 222 relative to the hub 224. The support 230 forms channels 231 through which gas flow can occur. Further, the hub 224 is slidably disposed within an annular slot 232 formed by the housing 202, for example by a shoulder 234. The slot 232 is fluidly connected to the HF port 210 and is sized to establish a fluidly-sealed relationship relative to the hub 224. Upon final assembly, then, the hub 224 is slidable within the slot 232, moving the obstruction body 222 from the closed position (pulse off) of FIG. 6A to the opened position (pulse on) of FIG. 6B, and vice-versa, in response to the gas flow/pressure acting on the trailing end 228. In this regard, a biasing member 236 (e.g., a spring) biases the hub 224 to the closed position, with the shoulder 234 providing a stop surface to movement of the hub 224 beyond the closed position of FIG. 6A (i.e., the shoulder prevents the hub 224 from moving leftward in FIG. 6A).

A pressure pulse imparted into the slot 232 acts upon the hub 224, generating a sufficient force to overcome that of the biasing member 236, causing the hub 224 to move within the slot 232 (rightward relative to the orientation of FIG. 6A). This movement is translated onto the obstruction body 222 via the support 230. Thus, in response to a positive pressure pulse within the slot 232 via the HF port 210, the baffle device 220 "moves" such that the obstruction body 222 is positioned away from the CPP port 212 as shown in the opened state of FIG. 6B. As the gas flow delivered to the slot 232 cycles "off," the biasing member 236 forces the hub 224, and thus the obstruction body 222, to return to the normal, closed position (FIG. 6A). The effect of the obstruction body 222 position upon gas flow through the CPP port 212 is described below. A wide variety of other constructions or mechanisms (powered or unpowered) can alternatively be employed to effectuate movement of the obstruction body 222 relative to the CPP port 212 that may, or may not, operate in response to pulsed gas flow from an external source. Thus, in some embodiments, the HF port 210 can be eliminated.

In some embodiments, the CPP port 212 is adapted for connection to a source of constant positive pressure gas, for example via tubing (not shown), and is fluidly connected to and/or forms a CPP nozzle 238. The CPP nozzle 238 generates jet flow, exiting at a nozzle end 240 that is otherwise fluidly associated or aligned with the obstruction body 222.

The entrainment port(s) 214 are open to ambient, and are fluidly associated with the nozzle end 240 of the CPP nozzle 238 at or "upstream" of the obstruction body 222. More particularly, the entrainment port(s) 214 is positioned such that high velocity gas flow generated at the nozzle end 240 causes ambient air to be drawn or entrained into the flow stream as described below.

The exhaust aperture(s) 216 is similar to the exhaust aperture 66 (FIG. 2) previously described, and may or may not be associated with a valve (not shown). Regardless, the exhaust aperture(s) 216 facilitates patient breathing into and out of the device 200 by providing an ambient opening to the primary passageway 206.

The optional nebulizer port 218 is adapted for fluid connection to a nebulizer ((not shown) but akin to the nebulizer previously described). Where provided, the nebulizer port 218 is preferably positioned such that aerosolized airflow into the primary passageway 206 does not directly impinge upon the flow diverter structure 208. In other words, the nebulizer port 218 is located along the primary passageway 206, fluidly between the mouthpiece 204 and the obstruction body 222, thus minimizing prevalence of aerosol knock-down. Alternatively, the nebulizer port 218 can be located at virtually any other location along the housing 202, and in other embodiments can be eliminated.

During use, the flow diverter structure 208 operates to selectively alter the volume of gas flow from the CPP port 212 to the primary passageway 206. As shown in FIG. 6B, during instances where the obstruction body 222 is discretely spaced from the CPP port 212 (and in particular the nozzle end 240), a jet flow of gas is delivered to the chamber 209 and impinges upon the obstruction body 222. Gas flow interfaces with the obstruction body 222 and flows through the channels 231, creating a vacuum effect, drawing in, or entraining, a significant level of ambient air (via the entrainment port(s) 214).

Conversely, when the obstruction body 222 is positioned in close proximity to the nozzle end 240 (FIG. 6A), gas flow from the nozzle end 240 is overtly restricted, such that minimal gas flow from the CPP port 240 occurs. As a result, there is little, if any, induced entrainment of ambient air from the entrainment port(s) 214.

In light of the above, high pressure is achieved with the arrangement of FIG. 6B, whereas a significantly lower pressure is attained with the arrangement of FIG. 6A. As the obstruction body 222 cycles between the positions of FIGS. 6A and 6B, then, high frequency oscillatory pressure is delivered to the patient via the primary passageway 206/mouthpiece 204. As a point of reference, the baffle device 220 can be configured to provide a known gap 242 in the engaged state (FIG. 6A) to achieve a desired minimum baseline pressure profile. Regardless, between pulses, the entrainment port(s) 214 and the exhaust aperture(s) 216 effectively allow the patient to breathe in and out of the device 200 without significant resistance.

Finally, where provided, aerosolized medication can be introduced into the gas flow being directed toward the patient via the nebulizer port 218. In this regard, the entrainment port(s) 214 and the exhaust aperture(s) 216 can be dimensionally balanced with valving (not shown) associated with the nebulizer port 218 ensuring that nebulizer entrainment is "activated" during the patient's inspiratory breath and between the oscillatory pulses that occur during a patient's inspiratory breath.

Figure 7A:
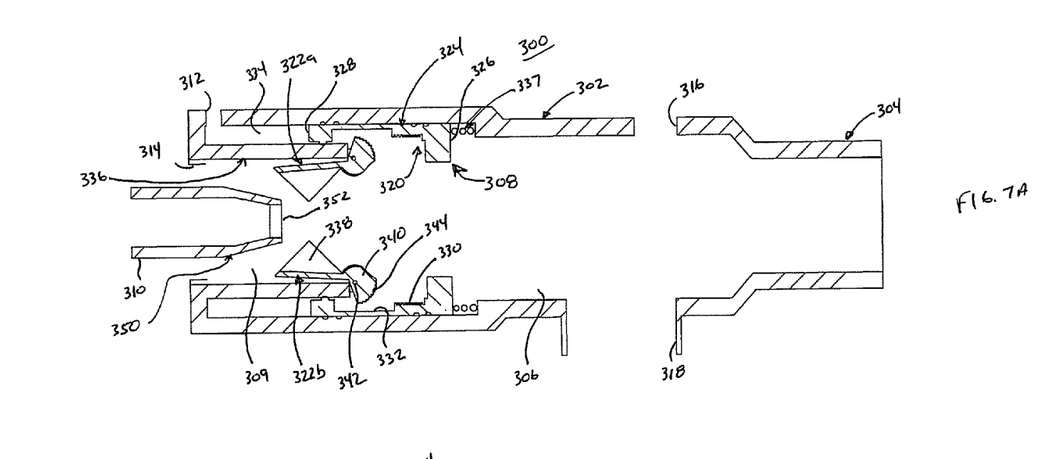
FIGS. 7A and 7B are simplified cross-sectional illustrations, with portions drawn schematically, of another embodiment respiratory therapy device.
Figure 7B:
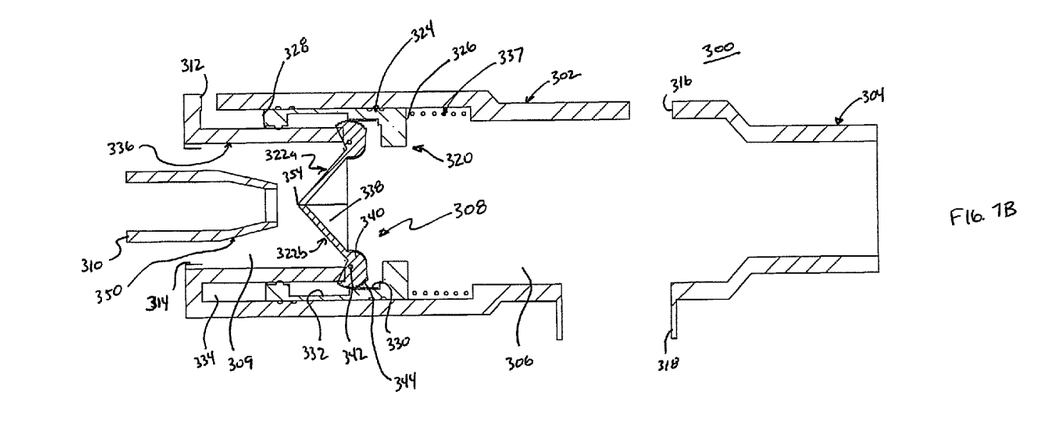

Another embodiment of a respiratory therapy device 300 in accordance with aspects of the present disclosure is shown in FIGS. 7A and 7B. The device 300 includes a housing 302 forming, maintaining, or connectable to a mouthpiece 304 (illustrated generally) through which a patient breathes. Gas flow to and from the mouthpiece 304 is provided via a primary passageway 306 defined by the housing 302. A flow diverter structure 308 is fluidly connected to the primary passageway 306 opposite the mouthpiece 304, and acts upon gas flow directed into a chamber 309 of the housing 308 via a CPP port 310. In some embodiments, the flow diverter structure 308 is fluidly connected to an HF port 312 through which an oscillatory pressure serves to actuate the flow diverter structure 308 as described below. In addition, the housing 302 forms or includes one or more entrainment ports 314 through which ambient air is drawn into and entrained within the flow stream generated at the diverter structure 308. Finally, the housing 302 optionally forms or includes one or more exhaust apertures 316 and/or a nebulizer port 318. As with previous embodiments, the nebulizer port 318, where provided, can be positioned adjacent the mouthpiece 304 and thus fluidly "downstream" of the flow diverter structure 308 to minimize aerosol knock-down.

With the therapy device 300 of FIGS. 7A and 7B, the flow diverter structure 308 includes a drive assembly 320 and obstruction bodies 322a, 322b. In general terms, the drive assembly 320 is slidably maintained within the housing 302, and operate to maneuver the obstruction bodies 322a, 322b between an opened position (FIG. 7A) and a closed position (FIG. 7B). The obstruction bodies 322a, 322b, in turn, are fluidly associated with the chamber 309/CPP port 310, and operate to alter the level of gas flow entering the primary passageway 306 from the chamber 309/CPP port 310, as well as the volume of ambient air entrained therein via the entrainment ports 314.

The drive assembly 320 includes an annular hub 324 having a leading end 326 and a trailing end 328. A toothed inner surface 330 is formed adjacent the leading end 326, and a recess 332 is formed between the toothed surface 330 and the trailing end 328. With this construction, the hub 324 is sized to be slidably received within a slot 334 formed by the housing 302, for example via an annular shoulder 336. In this regard, at least the trailing end 328 and the slot 334 are sized so as to establish a fluidly sealed relationship. Finally, the drive assembly 320 includes a biasing device 337 (e.g., a spring) positioned to bear against the leading end 326, biasing the hub 324 to the closed position of FIG. 7B.

The obstruction bodies 322a, 322b are configured to interface with the hub 324. For example, each of the obstruction bodies 322a, 322b includes a valve plate 338 and a drive segment 340. The drive segment 340 is pivotably or rotatably mounted within the housing 302 (e.g., via a pin 342), and forms a geared end 344. The geared end 344 is configured in accordance with the toothed surface 330 of the hub 324 such that when the hub 324 positions the toothed surface 330 adjacent the geared ends 344, the corresponding teeth mesh with one another and movement of the hub 324 is transferred to the drive segment 340, thereby causing movement of the corresponding obstruction body 322a, 322b. Thus, for example, movement of the hub 324 from the position of FIG. 7A to the position of FIG. 7B (i.e., leftward relative to the orientation of FIG. 7A) causes the obstruction bodies 322a, 322b to pivot or rotate from the opened position to the closed position as shown.

Finally, the flow diverter structure 308 includes one or more components that operate to selectively hold the obstruction bodies 322a, 322b in at least the open position of FIG. 7A and/or that bias the obstruction bodies 322a, 322b to naturally assume the opened position. For example, the flow diverter structure 308 can include one or more springs (not shown) that bias the obstruction bodies 322a, 322b to the open position, with a spring force constant of this spring(s) being less than that of the biasing member 337 otherwise acting upon the hub 324 such that the biasing member 337 is capable of readily moving the hub 324 from the opened position (FIG. 7A) to the closed position (FIG. 7B) without overtly being restricted by the interface with the obstruction bodies 322a, 322b. For example, a compression spring can be disposed between the valve plate 338 of the first obstruction body 322a and the corresponding, immediately adjacent segment of the shoulder 336 that biases the valve plate 338 toward the shoulder 336 segment; a torsional spring disposed between the valve plates 338; etc. In other configurations, the valve plates 338 can be magnetically attracted toward the corresponding shoulder 316 segment. Alternatively, the obstruction bodies 322a, 322b can be temporarily held in a multiplicity of positions (e.g., a ball-and-detent configuration), with the corresponding holding force being less than the spring constant force associated with the biasing member 337.

Upon final assembly, the hub 324 is slidably disposed within the slot 334. Pulsed flow delivered to the slot 334 via the HF port 312 causes the hub 324 to move. In particular, a pressure pulse imparted into the slot 334 acts upon the trailing end 328 of the hub 324, generating a sufficient force to overcome that of the biasing member 337, causing the hub 324 to move within the slot, transitioning from the closed position of FIG. 7B to the opened position of FIG. 7A. This movement is translated onto the obstruction bodies 322a, 322b via the geared interface between the toothed surface 330 and the geared end 344. In particular, movement of the hub 324 forces the obstruction bodies 322a, 322b to pivot about their corresponding pivot points (e.g., the pins 342), forcing the obstruction bodies 322a, 322b, and in particular the corresponding valve plates 338, toward the opened position of FIG. 7A. Alternatively and/or in addition, the obstruction bodies 322a, 322b may pivot or rotate slightly with movement of the hub 324; however, upon release of the geared engagement between the toothed surface 330 and the geared end 344 (i.e., the geared end 344 of each of the obstruction bodies 322a, 322b resides within the recess 332), the obstruction bodies 322a, 322b are no longer constrained by the hub 324, and thus freely pivot to the opened position via the corresponding spring(s) (not shown). Thus, in response to a positive pressure pulse within the slot 334, the obstruction bodies 322a, 322b are in an opened position relative to the chamber 309/CPP port 310 (i.e., present minimal gas flow obstruction between the chamber 309/CPP port 310 and the primary passageway 306).

Conversely, as the gas flow delivered to the slot 334 cycles "off," the biasing member 337 forces the hub 324 to return to the normal, closed position (FIG. 7B). With this movement, the hub 324 interfaces with the obstruction bodies 322a, 322b as described above, thereby actuating the hub bodies 322a, 322b to the closed position via geared engagement between the toothed surface 330 and the geared ends 344. The affect of the position of the obstruction bodies 322a, 322b upon gas flow through the CPP port 310 is described below. However, a wide variety of other constructions or mechanisms (powered or unpowered) can alternatively be employed to effectuate movement of the obstruction bodies 322a, 322b relative to the chamber 309/CPP port 310 that may, or may not, operate in response to pulsed gas flow from an external source. Thus, in some embodiments, the HF port 312 can be eliminated.

In some embodiments, the CPP port 310 is adapted for connection to a source of constant positive pressure gas, for example via tubing (not shown), and is fluidly connected to and/or forms a CPP nozzle 350. The CPP nozzle 350 generates jet flow, exiting at a nozzle end 352 that is otherwise fluidly associated or aligned with a center point 354 between the obstruction bodies 322a, 322b.

The entrainment port(s) 314 are open to ambient, and are fluidly associated with the nozzle end 352 of the CPP nozzle 350 at or "upstream" of the obstruction bodies 322a, 322b. More particularly, the entrainment port(s) 314 is positioned such that high velocity gas flow generated at the nozzle end 352 causes ambient air to be drawn or entrained into the flow of stream as described below.

The exhaust aperture(s) is similar to the exhaust aperture 66 (FIG. 2) previously described, and may or may not be associated with a valve (not shown). Regardless, the exhaust aperture(s) 316 facilitates patient breathing into and out of the device 300 by providing an ambient opening to the primary passageway 306.

The optional nebulizer port 318 is adapted for fluid connection to a nebulizer (not shown) but akin to the nebulizer previously described. Where provided, the nebulizer port 318 is preferably positioned such that aerosolized gas flowing into the primary passageway 306 does not directly impinge upon the flow diverter structure 308. In other words, the nebulizer port 318 is located along the primary passageway 306 fluidly between the mouthpiece 304 and the obstruction bodies 322a, 322b, thus minimizing prevalence of aerosol knock-down. Alternatively, the nebulizer port 318 can be located at virtually any other location along the housing 302, and in other embodiments can be eliminated.

During use, the flow diverter structure 308 operates to selectively alter the volume of gas flow from the chamber 309/CPP port 310 to the primary passageway 306. As shown in FIG. 7A, during instances where the obstruction bodies 322a, 322b are in the opened position, a jet flow of gas is delivered from the nozzle end 352 and passes through, but at least partially impinges upon, the obstruction bodies 322a, 322b and/or the reduced diameter defined by the leading end 326 of the hub 324. This interface draws in, or entrains, a significant level of ambient air via the entrainment port(s) 314.

Conversely, when the obstruction bodies 322a, 322b are in the closed position of FIG. 7B, gas flow from the nozzle end 352 is overtly restricted, such that minimal gas flow from the chamber 309/CPP port 310 to the primary passageway 306 occurs. As a result, there is little, if any, induced entrainment of ambient air from the entrainment port(s) 314.

In light of the above, high pressure is achieved with the arrangement of FIG. 7A, whereas a significantly lower pressure is attained with the arrangement of FIG. 7B. As the obstruction bodies 322a, 322b cycle between the opened and closed positions, then, high frequency oscillatory pressure is delivered to the patient via the primary passageway 306/mouthpiece 304. As a point of reference, the obstruction bodies 322a, 322b can be configured to provide a small gap (not shown) in at least the closed position to achieve a desired minimum baseline pressure profile. Regardless, between pulses, the entrainment port(s) 314 and the exhaust aperture(s) 316 effectively allow the patient to breath in and out of the device 300 without significant resistance.

Finally, where provided, aerosolized medication can be introduced into the gas flow being directed toward the patient via the nebulizer port 318. In this regard, the entrainment port(s) 314 and the exhaust aperture(s) 316 can be dimensionally balanced with valving (not shown) associated with the nebulizer port 318, ensuring the nebulizer entrainment is "activated" during the patient's inspiratory breath and between the oscillatory pulses that occur during a patient's inspiratory breath.

Although the present disclosure has been described with respect to preferred embodiments, workers skilled in the art will recognize that changes can be made in form and detail without departing from the spirit and scope of the present disclosure.

What is claimed is:
1. A respiratory therapy device comprising:
a housing defining a primary passageway having a patient interface side;
a flow diverter structure maintained by the housing in fluid communication with the primary passageway opposite the patient interface side, wherein the flow diverter structure is characterized by the absence of a venturi tube;
a high frequency pressure port maintained by the housing and configured for fluid connection to a source of oscillatory gas flow, the high frequency pressure port being fluidly associated with the flow diverter structure, and the high frequency pressure port comprising a nozzle configured to generate a jet gas flow from the source of oscillatory gas; and
an entrainment port maintained by the housing and openable to ambient air, the entrainment port being fluidly associated with the flow diverter structure;
wherein the device is configured such that flow characteristics of the jet gas flow from the source of oscillatory gas are altered upon interacting with the flow diverter structure to create a pressure drop for drawing in the ambient air through the entrainment port in delivering a percussive pressure therapy to the patient interface side of the primary passageway; and
wherein the flow diverter structure comprises a neck region having a tapering portion that tapers radially inward toward the primary passageway and a diverter body disposed within the tapering portion, the diverter body having a shape that tapers proximally toward the primary passageway from a distal end of the diverter body; and
a nebulizer port formed by the housing in fluid communication with the primary passageway at a location fluidly between the patient interface side and the flow diverter structure; and
a nebulizer fluidly connected to the nebulizer port.

2. The device of claim 1, wherein the flow diverter structure is fluidly positioned between the primary passageway and a chamber, the high frequency pressure port being fluidly open to the chamber.

3. The device of claim 2, wherein the entrainment port is fluidly open to the chamber.

4. The device of claim 2, wherein the nozzle terminates at a nozzle end, the nozzle end positioned to direct the jet gas flow toward the flow diverter structure.

5. The device of claim 4, wherein the neck region fluidly connects the chamber and the primary passageway.

6. The device of claim 5, wherein the neck region further comprises a constant diameter portion extending proximally from the tapering portion.

7. The device of claim 6, wherein the diverter body is positioned fluidly between the nozzle end and the constant diameter portion, the nozzle oriented such that the jet gas flow from the nozzle end impinges upon the diverter body and is directed toward the constant diameter portion.

8. The device of claim 6, further comprising:
a continuous positive pressure port which forms a continuous positive pressure nozzle projecting into the chamber, wherein the continuous positive pressure port is configured for fluid connection to a source of continuous positive pressure gas flow; and
wherein the continuous positive pressure nozzle and the high frequency nozzle converge at the flow diverter structure.

9. The device of claim 4, wherein an opening of the entrainment port to the chamber is located fluidly between the nozzle end and the flow diverter structure.

10. A respiratory therapy system comprising:
a respiratory therapy device including:
a housing defining a primary passageway having a patient interface side,
a flow diverter structure maintained by the housing in fluid communication with the primary passageway opposite the patient interface side, wherein the flow diverter structure is characterized by the absence of a venturi tube,
a high frequency pressure port maintained by the housing and fluidly associated with the flow diverter structure, the high frequency pressure port comprising a nozzle configured to generate a jet gas flow from a source of oscillatory gas, and
an entrainment port maintained by a housing and openable to ambient air, the entrainment port being fluidly associated with the flow diverter structure;
wherein the device is configured such that flow characteristics of the jet gas flow from the source of oscillatory gas are altered upon interacting with the flow diverter structure to create a pressure drop for drawing in the ambient air through the entrainment port in delivering a percussive pressure therapy to the patient interface side of the primary passageway; and
wherein the flow diverter structure comprises a neck region having a tapering portion that tapers radially inward toward the primary passageway and a diverter body disposed within the tapering portion, the diverter body having a shape that tapers proximally toward the primary passageway from a distal end of the diverter body; and
a nebulizer port formed by the housing in fluid communication with the primary passageway at a location fluidly between the patient interface side and the flow diverter structure; and
a nebulizer fluidly connected to the nebulizer port.

11. The system of claim 10, wherein the device further comprises a chamber formed by the housing and fluidly connected to the high frequency pressure port, and a continuous positive pressure port fluidly connected to the chamber, the system further comprising:
a source of continuous positive pressure gas flow fluidly connected to the continuous positive pressure port.

* * * * *